United States Patent [19]

Perry et al.

[11] Patent Number: 4,933,467
[45] Date of Patent: Jun. 12, 1990

[54] PREPARATION OF IMIDES

[75] Inventors: Robert J. Perry; S. R. Turner, both of Pittsford, N.Y.

[73] Assignee: Eastman Kodak Company, Rochester, N.Y.

[21] Appl. No.: 405,151

[22] Filed: Sep. 11, 1989

Related U.S. Application Data

[63] Continuation-in-part of Ser. No. 297,788, Jan. 17, 1989.

[51] Int. Cl.$^5$ ............................................. C07D 209/48
[52] U.S. Cl. ..................... 548/476; 546/200; 546/201; 546/208; 548/539; 560/97; 560/206; 562/406
[58] Field of Search ............................ 548/476, 539; 260/544 A; 546/200, 201, 208; 560/97, 206; 562/406

[56] References Cited

PUBLICATIONS

Yoneyama et al., Macromolecules (1988) 21, pp. 1908–1911.
R. F. Heck, Palladium Reagents in Organic Syntheses, Academic Press, New York, N.Y. (1985) pp. 348–359.
Mori et al., Heterocycles 13, (1979) pp. 329–332.

Primary Examiner—Anton H. Sutto
Assistant Examiner—D. D. Carr
Attorney, Agent, or Firm—Robert A. Linn

[57] ABSTRACT

Cyclic imides are prepared by reacting carbon monoxide with an ortho dihalide aromatic compound or a cis-1,2-vinyl dihalide and an amide in the presence of palladium catalyst and a base. The process is preferably conducted in the presence of a dipolar aprotic solvent as a liquid reaction medium.

18 Claims, No Drawings

PREPARATION OF IMIDES

CROSS-REFERENCE TO RELATED APPLICATION

This application is a continuation-in-part of application Ser. No. 297,788, filed Jan. 17, 1989.

FIELD OF THE INVENTION

This invention relates to cyclic imides and to processes for their preparation. The imides may be monomeric, oligomeric, or polymeric. The processes comprise palladium catalyzed carbonylations. Other catalysts can be used.

RELATED ART

Yoneyama et al, Macromolecules (1988), 21, pp. 1908–1911, discloses the synthesis of aromatic polyamides by palladium-catalyzed polycondensation of aromatic dibromides, aromatic diamines, and carbon monoxide.

The literature relating to the carbonylation of aromatic halides, and the formation of amides and other compounds by such a route, is summarized in Heck, R. F., *Palladium Reagents in Organic Syntheses,* Academic Press, New York, N.Y. (1985) pp. 348–359. The preparation of cyclic imides by the process of this invention is not suggested by the above references.

Mori et al, *Heterocycles* 13, 329–332 (1979) discloses formation of monomeric cyclic imides and quinolone by the palladium catalyzed carbonylation of aryl and vinyl monobromides having an amine or amide group on a carbon atom adjacent to the carbon substituted with the bromide radical. The reference does not disclose the reaction of dibromides or diiodides.

SUMMARY OF THE INVENTION

This invention provides a method for the preparation of cyclic imides. The products may be monomeric, oligomeric, or polymeric. The products may also contain amide groups and other functional groups.

The process is illustrated by the following equations depicting the preparation of N-phenylphthalimide from o-diiodobenzene, aniline, and carbon monoxide. The illustrated process is conducted in the presence of palladium tetrakis(triphenylphosphine) (PdL$_4$), dimethylacetamide (DMAc), and 1,8-diazobicyclo-[5,4,0]undec-7-ene (DBU). The DMAc is used as a solvent; the DBU is a base for neutralizing by-product hydrogen halide. One possible mechanism is depicted by the following equations:

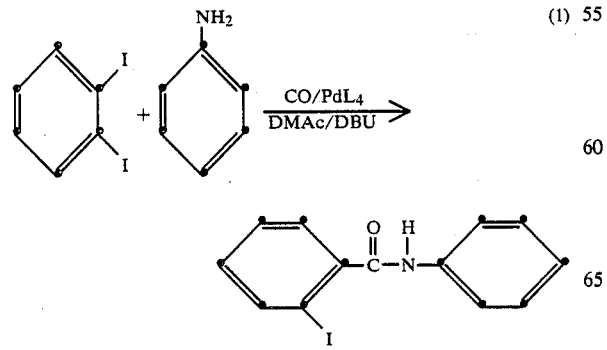

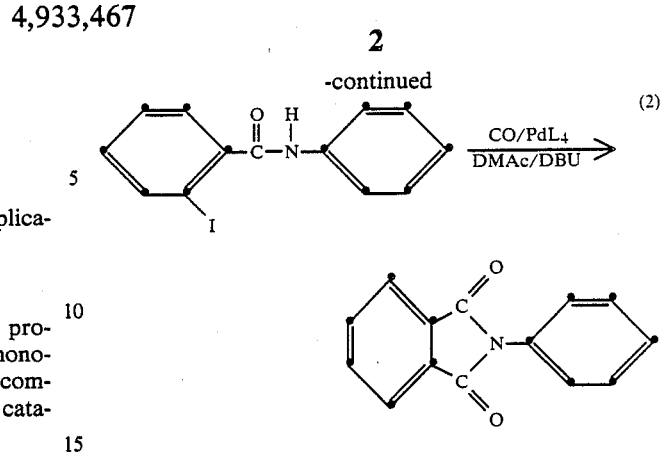

Although not bound by any theory, it is believed that the reactions depicted by Equations (1) and (2) may both proceed through an unisolated intermediate, formed by insertion of

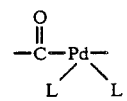

between the ring and the halide radical. Thus, for example, it is believed that the intermediate formed in Equation (2) has the formula:

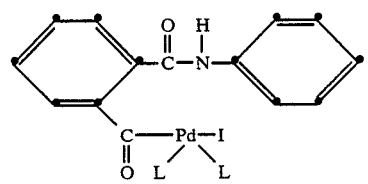

where L is a ligand such as carbon monoxide or triphenylphosphine. The above process suggests that it is not necessary to use an aromatic orthodihalide reactant (i.e., an aryl compound with 1,2-dihalofunctionality) as depicted in the above example. More specifically, it suggests that one may use a cis-1,2-dihalovinyl compound, and react it with CO and a primary amine as illustrated by the following unbalanced, simplified equation:

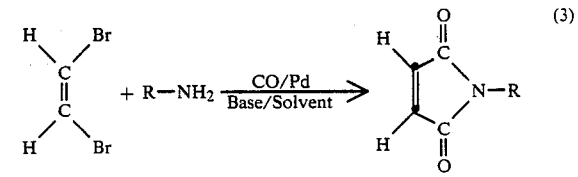

Oligomeric or polymeric products can be produced by reactions similar to the above; for example, by reacting carbon monoxide with a compound having two primary amine groups and a compound having two pair of halogen atoms. Similarly, oligomers or polymers can be made by polymerizing a compound having an amino group and a pair of adjacent, aromatic or vinylic halogens in the presence of CO, palladium catalyst, base, and solvent.

The monomeric, oligomeric, and polymeric compounds can be used as chemical intermediates. The oligomeric and polymeric imides have the utilities known for these classes of materials. For example, the polyimides can be used an engineering plastics.

It will be noted from the above equations that the process of this invention for preparing polyimides does not employ reactants commonly used in the art for preparing such materials. Some of the prior art reactants, e.g., anhydrides are susceptible to hydrolysis. The reactants used in the present process are not. Furthermore, it will also be noted that water is not formed as a by-product in the instant process. Hence, the process of this invention has inherent advantages over known, prior processes for polyimide formation.

DESCRIPTION OF PREFERRED EMBODIMENTS

This invention comprises (1) a process for the preparation of a cyclic imide, said process comprising reacting carbon monoxide and a primary amine with a vicinal organo dihalide, i.e., a dihalide which has two halogen radicals (selected from bromide and iodide) on adjacent carbon atoms, said dihalide selected from the class consisting of aryl ortho dihalides and cis-1,2-dihalovinyl compounds; said process being conducted in the presence of a catalytic quantity of a palladium catalyst, an ether or dipolar aprotic solvent, and a base for neutralizing by-product hydrogen halide.

Thus, this invention has embodiments in which carbon monoxide is reacted with an organic compound containing only one, or two or more dihalo functions, said functions being selected from the ortho dihalide and cis-1,2-dihalovinyl functionalities described in (1) above, and with a primary diamine, to form an oligomeric or polymeric cyclic imide having Formula I below;

These reactions are conducted in the presence of a catalyst, solvent, and base as mentioned above.

The preferred processes for preparing oligomers and polymers employ difunctional starting materials. Products made from such starting materials are generally linear and tractable. If one or more of the reactants are trifunctional, non-linear products can be formed. Such products generally are less tractable, i.e., less capable of producing useful end products. Hence, in many instances, processes of this invention which utilize trifunctional starting materials are less preferred.

Method (1) provides monomeric cyclic imides if one of the reactants, either the aromatic halide or the primary amine, is monofunctional, i.e., has only one functional group to react according to the process of this invention. Similar considerations hold for method (2).

Cyclic imide oligomers and polymers produced by the process of this invention have the formula:

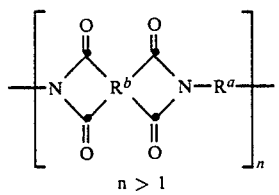

(I)

n > 1 wherein $R^a$ is the moiety from the primary diamine reactant and $R^b$ is the moiety derived from the halide reactant having two pair of adjacent halide radicals.

In the above formula, n is an integer having a value of 2 to about 500 or higher, more preferably from 2 to about 350. For the purpose of this invention, when the value of n is from 2 to about 10, the products are referred to as "oligomers"; when the value of "n" is higher, the products are referred to as "polymers".

The reactants from which these products are derived are discussed and illustrated below.

Some aryl ortho dihalides useful in this invention as starting materials have the formula:

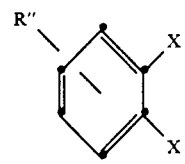

wherein each X is independently selected from bromine and iodine, and R" is an inert substituent.

As set forth more fully below, the dihalide need not be a benzenoid compound as depicted above. Rather, it may be a dihalide derivative of a fused ring compound. Alternatively, the dihalide may have two or more aryl groups bonded together or linked by a linking group. The dihalides may have additional substitution.

For example, in a fused ring compound, or in a compound having two linked aryl groups, or two bridged aryl groups, there may be two pair of halogens ortho to each other. Reaction of such a compound with a compound having a plurality of primary amino groups according to this invention will yield a polymeric or oligomeric cyclic imide.

The reactants of this invention may have a pair of ortho halogens and a primary amino substituent ($-NH_2$) in the molecule. When these materials are reacted with CO according to this invention, they can form a polymeric or oligomeric substance with imide groups.

From the above it can be seen that a wide variety of halides can be reacted according to this invention. They may be exemplified by compounds having one of the following general formulas wherein X is bromide or iodide and Y is carbon or a hetero atom such as, but not limited to, oxygen, nitrogen, sulfur, phosphorous, silicon, etc.

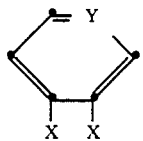

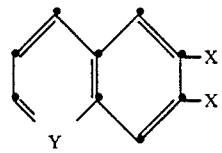

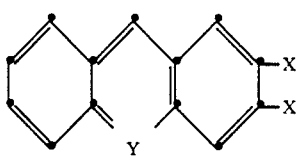

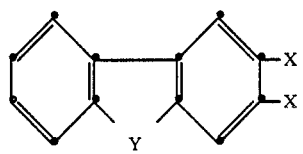

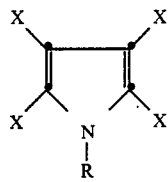

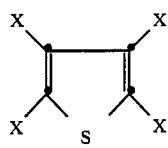

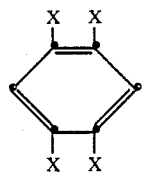

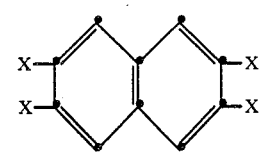

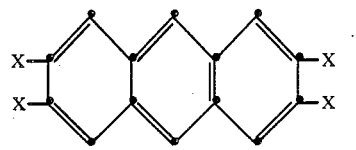

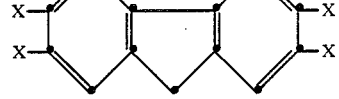

It will be apparent to a skilled practitioner that ortho dihalo derivatives of other fused ring systems are also applicable in this invention, and that the ortho halogen pair may be in positions other than illustrated above.

In addition, the pair of ortho halogens may be within compounds having two or more isolated aryl rings which are bonded together, such as ortho dihalo derivatives of biphenyl and terphenyl. Also, the pair of ortho halogens may be substituted on rings within compounds having two or more fused ring systems that are bonded together or that have a fused ring system bonded to a benzenoid nucleus as in the following examples:

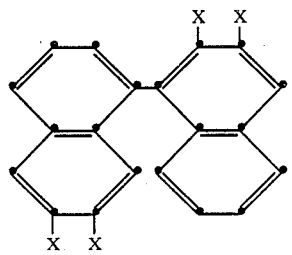

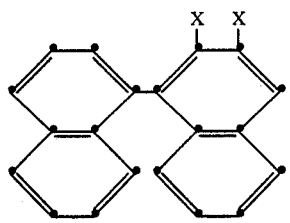

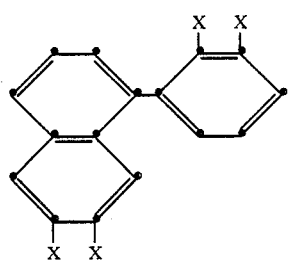

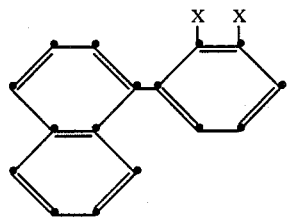

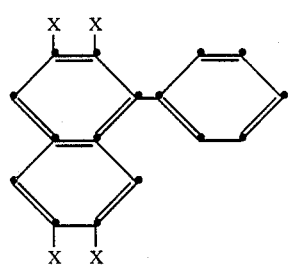

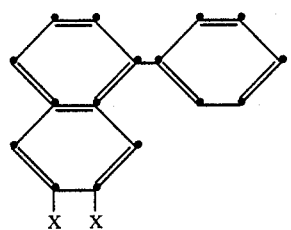

In accordance with the description above, additional reactants employed in this invention are exemplified by the following compounds:

Additional reactants useful in this invention are illustrated by:

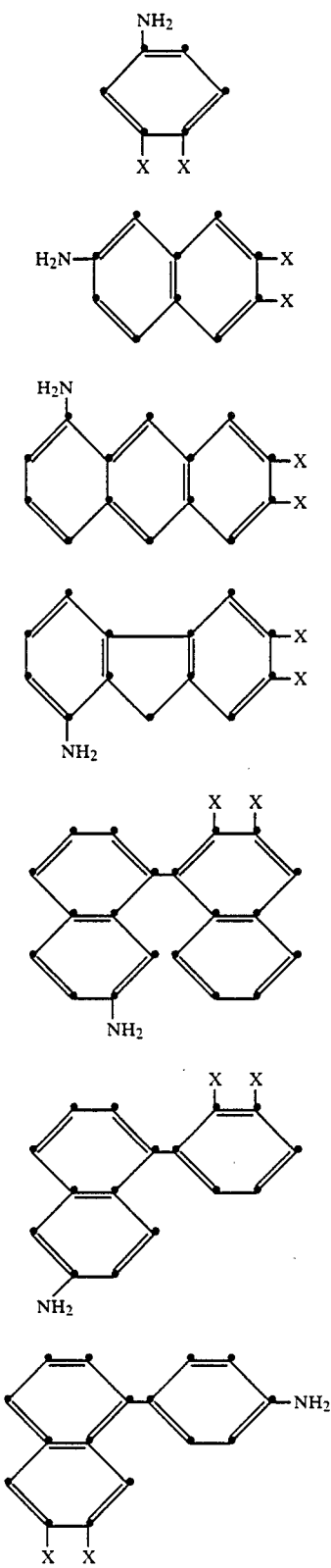

$-\underset{\underset{CH_3}{|}}{\overset{\overset{CH_3}{|}}{Si}}-$, $-\overset{\overset{O}{\|}}{C}-$, $-\overset{\overset{O}{\|}}{C}-O-$, $-\underset{\underset{CH_3}{|}}{\overset{\overset{CH_3}{|}}{C}}-$, $-\overset{\overset{O}{\|}}{C}-HN-$, —CH$_2$—, and —CH$_2$—(CH$_2$)$_n$—CH$_2$—, wherein n is from about 1 to about 6 or higher, and the like. Such reactants are illustrated by the following formulas, wherein Y' is a bridging group of the type illustrated above or phenylene, vinylene, carbonate, or $-\underset{\underset{CF_3}{|}}{\overset{\overset{CF_3}{|}}{C}}-.$ In addition, the bridging group Y' can bridge a benzene nucleus with a fused ring system, or two fused ring systems:

Reactants analogous to the above can have the rings or fused ring systems connected by a bridging group rather than bonded together by a carbon-to-carbon bond. Typical bridging groups are: —O—, —S—, —SO$_2$—, Other fused ring systems similar to those illustrated above can be linked by a bridging group Y', and substituted with a pair of ortho halogens, or two or more pair of ortho halogens, or one pair of ortho halogens and one ortho halogen or —NH$_2$ group.

Of the dihalo reactants mentioned above, it is preferred to use ortho diodo aromatic compounds.

Preferred ortho diiodo aromatic compounds useful as reactants are illustrated by:

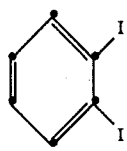

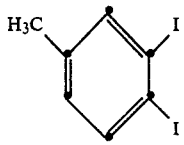

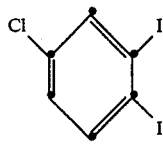

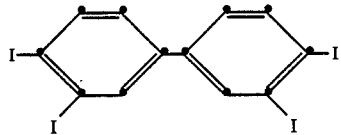

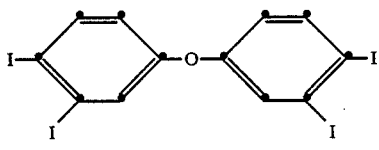

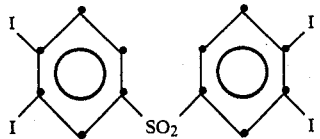

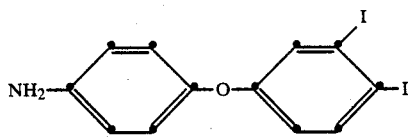

Cis-vinyl dihalides have been mentioned above as reactants in this invention. The vinyl linkage may be in a chain or ring, e.g., in cyclopentene. Two cyclopentene groups can be bonded together by a carbon-to-carbon bond, or linked by a bridging group. Alternatively, the cyclopentene ring can be a substituent on an aryl nucleus as in

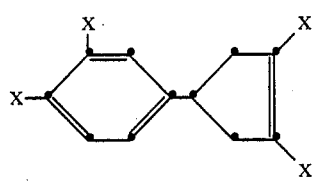

The cyclopentene ring can be substituted with an amino group —$NH_2$, or by an alkenyl radical having a vinyl bromide or iodide radical.

Preferably, the amine reactant is an alkyl or aromatic amine. It can be aniline, or alternatively be a primary or secondary amine derivative of one of the fused or bridged ring systems of the type illustrated above. Similarly, there may be two or more primary amino groups substituted on a benzenoid nucleus, or on a fused ring system or a bridged ring system.

Aliphatic primary amines can be used in this process. They may be saturated or unsaturated. They may also comprise one or more (non-aryl) rings or be acyclic. Preferably, the aliphatic amines are alkyl primary or secondary amines wherein the alkyl group or groups have up to about 10 carbon atoms. The alkyl groups may be branched or unbranched. Preferably the amines are liquids or solids that are soluble or dispersible in the reaction mixture.

Compounds having two or more primary amino groups within the molecule are illustrated by the following compounds:

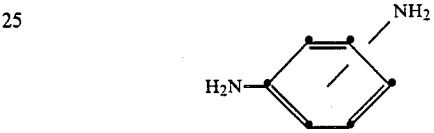

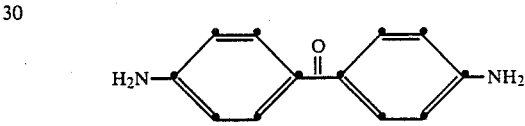

In a preferred embodiment, polyiodides are used as the dihalo reactant. Such materials can be produced as described in U.S. Nos. 4,746,758, 4,792,641 and 4,792,642.

The process of this invention is not limited to any aromatic system. Thus, the invention can be applied to any polyiodoaromatic which reacts under the reaction conditions employed to give an imide.

Suitable aromatic compounds include hydrocarbon-aromatics, nitrogen containing aromatics and sulfur-containing aromatics and oxygen-containing aromatics such as dibenzofuran. Typical hydrocarbon aromatics include benzene and biphenyl, and condensed ring aromatics such as naphthalene and anthracene. Sulfur-containing aromatics include thiophene and benzothiophene. Nitrogen-containing aromatics include N-substituted pyrroles and carbazoles. The iodo substituents may be bonded to substituted or unsubstituted aromatics. Substituted aromatics are exemplified by compounds such as aryl sulfones, diaryl ethers, diaryl carbonyls, diaryl sulfides, and the like.

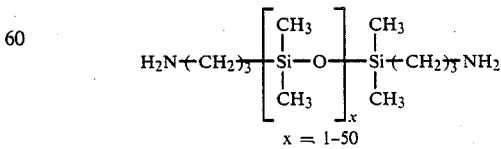

x = 1–50

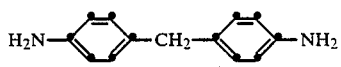

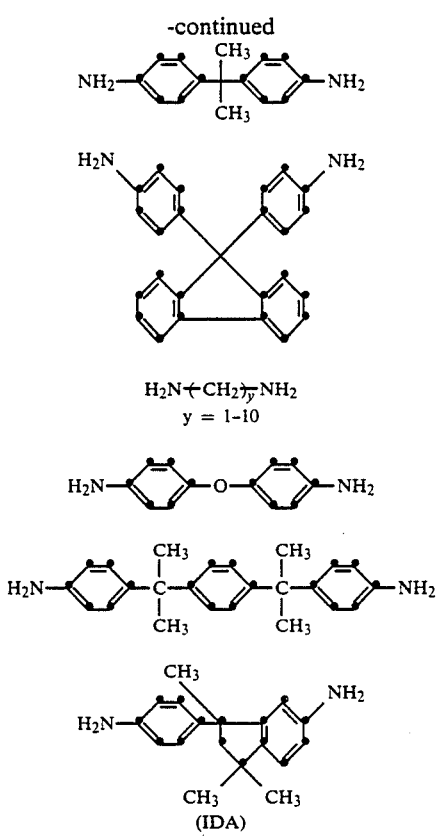

The compound illustrated by the last structural formula above can be made by dimerizing alpha methylstyrene, nitrating the dimerized product, and then reducing the nitro groups to form the amino groups. The type of monomer illustrated by the last structural formula is important for a number of reasons. First, the molecule is not symmetrical, and the two functional groups are bonded to two different moieties. Second, the two rings are orthogonal, i.e. not in the same plane. These structural characteristics tend to yield polymers with less structural regularity and less crystallinity. Thus, the polymers have more solubility in organic solvents such as the solvents used as reaction media in the process of the present invention. With greater solubility, there is a lessened tendency for the polymer to prematurely precipitate from solution while it is being formed. Consequently, there is an increased ability to prepare imide products with higher molecular weight.

As can be seen by the above description, a wide variety of dihalo and amino reactants can be used in the processes of this invention. Preferably, such reactants are "stable" under the reaction conditions employed, i.e., they do not decompose to an unacceptable extent during the process of this invention. The organic materials used in this invention are also "suitable reactive", i.e., the process of this invention without entering into an unacceptable amount of undesirable side reaction(s). Thirdly, the organic reactants used in this invention should be "sterically suitable", i.e., that they not be so bulky as to unduly retard the reaction by steric hindrance. Examples of such reactants have been given above.

The amine and halide reactants are contacted with carbon monoxide. The CO may be at atmospheric pressure or at a higher pressure. Carbon monoxide pressures in the range of from about 1 to about 200 atmospheres or higher can be used in the process.

Pressures lower than atmospheric can be used if desired, but generally do not confer any advantage.

The process proceeds well when the reactants are contacted in stoichiometric amounts. However, it is not necessary to use stoichiometric quantities. An excess of one or more reactants can be used to control the average degree of polymerization, $\overline{DP}$. A convenient amount of excess is preferably used.

It is convenient to add an excess of carbon monoxide to the reaction zone. The excess of CO need not be measured; one may merely pressurize the vessel with CO to the desired reaction pressure.

When one of the organic reactants is used to excess, it is preferably used in an amount of from 1.001 to about 5 times the molar amount required by stoichiometry.

The process of this invention is conducted in the presence of a liquid reaction medium to facilitate contacting the reactants. A wide variety of organic compounds can be used for this purpose so long as the reaction medium is "inert", i.e., does not enter into the reaction in an undesired way. It is preferred that the reaction medium dissolve the reactant(s) to an appreciable extent. For preparation of monomeric cyclic imides, an ether solvent can be used. A preferred solvent of this type is tetrahydrofuran or diglyme (2-methoxyethyl ether), or glyme (1,2-dimethoxy ethane). For preparation of oligomeric and polymeric products, a dipolar aprotic solvent is preferentially employed. Such solvents are characterized by the lack of acidic, easily abstractable hydrogens and are highly polar molecules. Typical dipolar aprotic solvents are dimethyl formamide, dimethylacetamide, dimethylsulfoxide, hexamethylphosphoramide, and the like.

The amount of liquid reaction medium is not critical. Generally, one uses enough medium to facilitate the reaction. There is no real upper limit on the amount of reaction medium employed. However, practical limits are imposed by the size of the reaction vessel, the ease of separation of product(s) from the reaction medium, cost, and similar considerations. Generally, the amount of liquid reaction medium employed is within the range of from about 0.1 to about 800 volumes based on the volume of halo or vinyl aromatic employed.

The process of this invention is conducted in the presence of a catalyst. The catalyst is preferentially a palladium compound, where palladium is present in the zerovalent or divalent state. Other transition metal catalysts, e.g., nickel and cobalt catalyst can be used. The palladium catalysts generally have one or more ligands bonded to the palladium atom(s) by ionic or covalent bonds. Simple palladium satls such as $PdX'_2$ wherein X' is Cl, Br or I can be used. Other representative palladium catalysts are listed below:

TABLE I

| Palladium Catalysts | |
|---|---|
| $Pd^{+2}$ | |
| $PdX_2$ | X = Cl, Br, I |
| $PdX_2L_2$ | X = Cl, Br, I |
| | L = $R_3P$, where R = alkyl or aryl |
| $Pd(OAc)_2$ | OAc = acetate |
| $Pd(OAc)_2L_2$ | OAc = acetate |
| $PdCl_2(RCN)_2$ | R = $CH_3$, Phenyl |
| $PhPdXL_2$ | X = Br, I |
| $PdCl_2(COD)_2$ | COD = cis,cis-1,5-cyclooctadiene |
| $Pd(acac)_2$ | acac = 2,4-pentanedionate |
| $Pd^{(o)}$ | |

TABLE I-continued
Palladium Catalysts

PdL$_4$
L = R$_3$P where
R = alkyl or aryl

Pd (Ph Ph)$_3$

It is contemplated that similar results can be obtained when other transition metal catalysts are employed, such as those containing nickel, rhodium, or ruthenium.

A catalytic amount of catalyst is employed. By "catalytic amount" is meant an amount of catalyst which catalyzes the reaction to the desired extent. Generally, the amount of catalyst is at least about 0.05 mole percent based on the amount of aryl or vinyl halide. There is no real upper limit on the amount of catalyst, this being defined by secondary conditions such as cost and ease of separation of the catalyst from products and unreacted reactants. A preferred catalytic amount is from about 0.005 to about 0.20 moles per mole of aryl or vinyl halide, more preferably from about 0.02 to about 0.10 mole per mole of halide reactant.

The process of this invention is preferably conducted in the presence of a base to neutralize by-product hydrogen halide. The base may be a tertiary amine such as tributylamine, pyridine, 1,8-diazobicyclo[5,4,0]-7-undecene (DBU) or have the formula:

NR$_3$ wherein each R is independently selected from lower alkyl groups having from about 2 to about 6 carbon atoms. The base may be immobilized on a cross-linked polymer such as cross-linked poly(vinylpyridine) beads. Alternatively, the base may be another type of basic substance which does not react with the reactants, e.g., a metal carbonate such as K$_2$CO$_3$ or a metal hydroxide such as Ca(OH)$_2$. Generally, one employs at least enough base to react with the by-product HX produced. An excess can be used, if desired.

As with the reactants, solvents and catalysts, a skilled practitioner will recognize that the exact structure of the base is not critical, and the examples of compounds set forth above are merely illustrative and not-limiting examples of materials that can be used in this invention. A skilled practitioner will recognize that other materials can be substituted in this invention to achieve similar results.

The process of this invention is preferably conducted at a temperature within the range of from about ambient to about 250° C. A preferred temperature range is from about 60° C. to about 160° C. A skilled practitioner will recognize that the reaction temperature is not critical, and that temperatures outside this range can be employed, if desired. Generally, one selects a reaction temperature which affords a reasonable rate of reaction and which does not give an undue amount of decomposition of products or reactants.

The reaction time is not a truly independent variable, but is dependent at least to some extent based on the other reaction parameters selected such as reactivity of the reactants, activity, and amount of catalyst, reaction temperature, pressure, and similar variables. Generally speaking, reaction times within the range of from about 0.1 to about 100 hours are used.

EXAMPLE 1

Preparation of N-phenylphthalimide

To a dry 3-neck, 25 mL round bottom flask equipped with a Teflon ® resin coated stir bar, a balloon filled with carbon monoxide and a vacuum/argon inlet was placed o-diiodobenzene (320 mg, 0.97 mmol), aniline (90 mg, 0.97 mmol), palladium tetrakis(triphenylphosphine) (PdL$_4$) (56 mg, 0.048 mmol=5%) and N,N-dimethylacetamide (DMAc, 2.9 mL). The mixture was stirred and degassed three times with argon, and then the argon atmosphere was replaced with carbon monoxide by three successive evacuations of the flask. The flask was then immersed in a 115° C. oil bath and heated until the reagents had dissolved. Then 1,8-diazobicyclo[5,4,0]undec-7-ene (DBU, 320 μl, 2.13 mmol) was added by syringe. After about 12 hours the product was produced in quantitative yield as determined by gas chromatography. The mixture was cooled, diluted with chloroform, extracted with water, dried over MgSO$_4$, precipitated with methanol, collected by filtration, and dried in vacuo to give 40 mg product (19%). Much of the product remained in the filtrate.

EXAMPLE 2

The preparation of N-phenylphthalimide described above can be improved by increasing the carbon monoxide pressure from one atmosphere to 90 psi. Thus, to a dry 60 mL Fisher-Porter ® bottle equipped with a Teflon coated stir bar and a head fitted with a pressure gauge, a syringe inlet, a gas inlet, and a pressure release valve was added α-diiodobenzene (200 μl, 1.53 mmol), aniline (140 μl, 1.53 mmol), PdCl$_2$L$_2$ (65 mg, 0.092 mmol, 6%), triphenyl phosphine (49 mg, 0.184 mmol), and DMAc (7.7 mL). The contents of the bottle were degassed and placed under one atmosphere of carbon monoxide and heated to 115° C. in an oil bath. When the contents of the bottle had dissolved, DBU (550 μl, 3.69 mmol) was added by syringe and the bottle charged to 90 psi with carbon monoxide. After two hours, the product was produced in quantitative yield as determined by GC as compared to 12 hours under one atmosphere.

EXAMPLE 3

The preparation of N-phenylphthalimide can also be improved by increasing the temperature from 115° C. to 150° C. Thus, at 90 psi, 6% PdCl$_2$L$_2$ and 150° C., quantitative product formation occurs in 45 minutes rather than 2 hours at 115° C.

The catalyst PdL$_4$ can be replaced with chloride (PdCl$_2$L$_2$) by adding two equivalents of triphenyl phosphine.

EXAMPLE 4

Preparation of N-phenylphthalimide

A flask equipped as in Example 1 was charged with o-dibromobenzene (270 mg, 1.14 mmol), aniline (106 mg, 1.14 mmol), PdL$_4$ (66 mg, 0.057 mmol=5%) and DMAc (3.5 mL). When the contents had dissolved, DBU (380 μl, 2.52 mmol) was added and the reaction was monitored by gas chromatography (GC). After 72 hours at 115° C. approximately 80% product had been formed as determined by GC.

EXAMPLE 5

Preparation of N-hexylphthalimide

A flask equipped as in Example 1 was charged with o-diiodobenzene (360 mg, 1.76 mmol), n-hexylamine (179° mg. 1.76 mmol), PdL₄ (126 mg, 0.109 mmol=6.2%) and DMAc (4 mL). Then DBU (633 μl, 4.23 mmol) was added. The reaction was allowed to proceed at 115° C. for 19.5 hours at which time there was no more starting iodide or amine as seen by GC. Isolation by dilution with chloroform, extraction with water, drying with MgSO₄, concentration and standing gave a crystalline solid which was washed with hexane to give 75 mg product (16%).

EXAMPLE 6

Preparation of N,N'-bis(m-tolyl)pyromellitimide

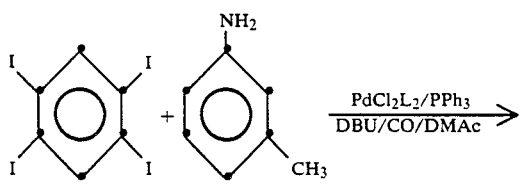

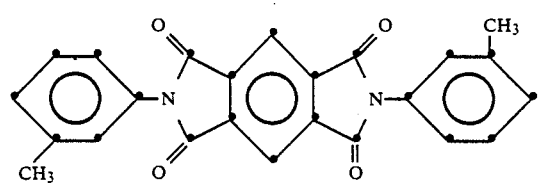

To a Fischer-Porter bottle was added 1,2,4,5-tetraiodobenzene (TIB 1.357 g, 2.33 mmol), m-toluidine (500 μl, 4.67 mmol), bis(triphenylphosphine)palladium (II) chloride (PdCl₂L₂, 98 mg, 0.14 mmol), triphenylphosphine (PPh₃, 73 mg, 0.28 mmol) and N,N-dimethylacetamide (DMAc, 14.2 mL). The reaction mixture was degassed and placed under 30 psi carbon monoxide (CO) and heated to 115° C. When the contents of the vessel had dissolved 1,8-diazabicyclo[5.4.0]undec-7-ene (DBU, 1.67 mL, 11.18 mmol) was added by syringe and the vessel was charged to 90 psi CO. After 21 hours the contents of the flask were allowed to cool to room temperature ater which diethylether was added to the mixture. The solid which precipitated was collected by filtration and recrystallized from DMAc to give the product (370 mg, 40%) as a yellow microcrystalline solid, mp 340°-341° C. IR(KBr) 1770, 1720, 1705, 1480, 1380, 1365, 1110, 835, 780, 725 cm⁻¹.

EXAMPLE 7

Preparation of Aromatic Poly(imide)

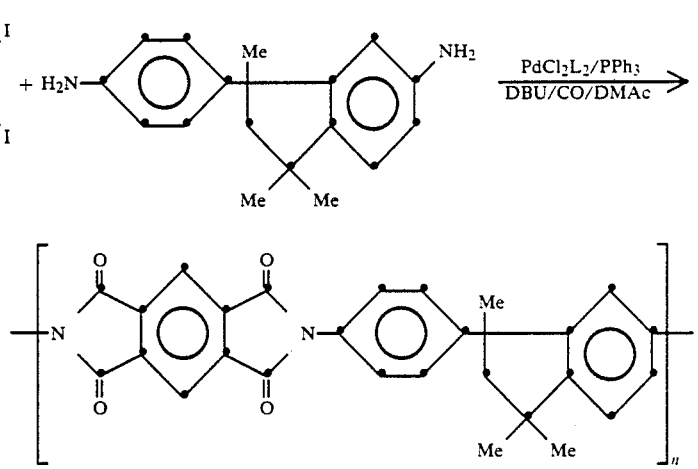

A Fischer-Porter bottle was charged with TIB (2.455 g, 4.22 mmol), (IDA) (1.124 g, 4.22 mmol), PdCl₂L₂ (178 mg, 0.253 mmol), PPH₃ (133 mg, 0.506 mmol) and DMAc (21.1 mL). After degassing, heating to 115° C., dissolution of reagents and subsequent addition of DBU (3.03 mL, 20.26 mmol) the vessel was charged with 90 psi CO and the reaction was allowed to proceed for 23 hours. At the end of this time the contents of the vessel were precipitated into methanol, isolated by filtration, washed with methanol, and dried in vacuo to give 1.8 g polymer (95%) as a dark solid. IV (0.25% in DMAc @ 25° C.)=0.56. $\overline{Mn}$=17,300, $\overline{Mw}$=281,000. (by SEC, size exclusion chromatography) IR(KBr) 1775, 1720 cm⁻¹(imide C=O).

EXAMPLE 8

Preparation of Aliphatic Poly(imide)

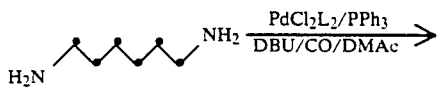

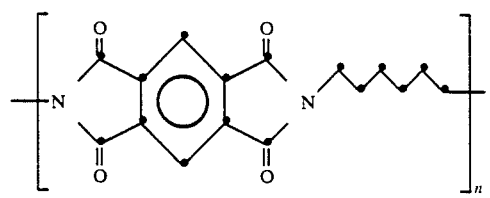

A Fischer-Porter bottle was charged with TIB (2.320 g, 3.99 mmol), 1,6-diaminohexane (463 mg, 3.99 mmol), PdCl₂L₂ (84 mg, 0.12 mmol), PPh₃ (63 mg, 0.24 mmol)

and DMAc (12.1 mL). After degassing, heating to 120 C., dissolution of reagents and subsequent addition of DBU (2.86 mL, 19.15 mmol) the vessel was charged with 80 psi CO and the reaction was allowed to proceed for 23 hours. At the end of this time the contents of the vessel were precipitated into methanol, isolated by filtration, washed with methanol and dried in vacuo to give 940 mg (79%) polymer as a dark solid. IR(KBr) 1770, 1710 cm$^{-1}$ (imide C=O). IV (0.25% in conc. H$_2$SO$_4$ @ 25° C.)=0.42.

EXAMPLE 9

Preparation of Aromatic Poly(imide)

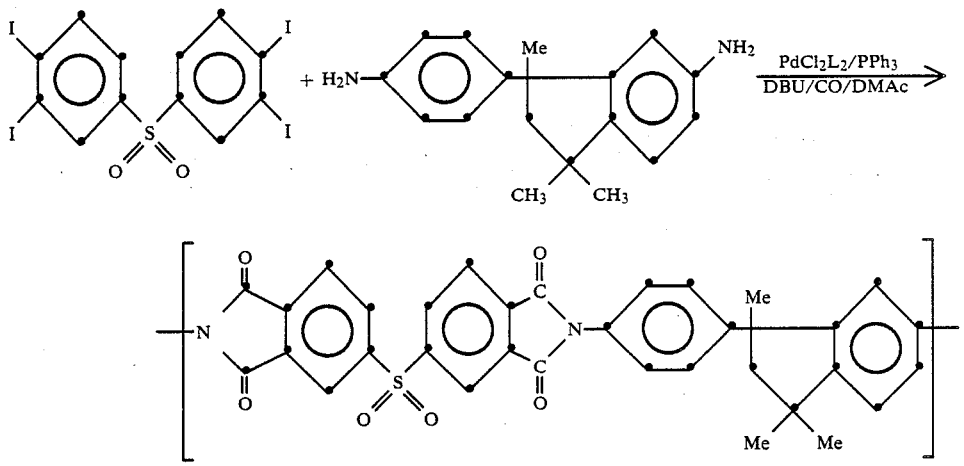

A Fischer-Porter bottle was charged with 3,3′,4,4′-tetraiododiphenylsulfone (1.508 g, 2.09 mmol), (IDA) (0.556 g, 2.09 mmol), PdCl$_2$L$_2$ (44 mg, 0.063 mmol), PPh$_3$ (33 mg, 0.126 mmol) and DMAc (10.4 mL). After degassing, heating to 120 C., dissolution of reagents and subsequent addition of DBU (2.86 mL, 19.15 mmol) the vessel was charged with 95 psi CO and the reaction was allowed to proceed for 22 hours. At the end of this time the contents of the vessel were filtered through a filter aid, precipitated into methanol, washed with methanol and dried in vacuo to give 680 mg polymer (55%) as a gray solid. IV (0.25% in DMAc @ 25 C.)=0.09. IR(KBr) 1780, 1720 cm$^{-1}$ (imide C=O).

In the process of the above examples, the dimethyl acetamide solvent can be substituted with an ether such as those named above, or by N,N-dimethyl formamide, hexamethylphosphoramide, dimethylsulfoxide, 1,3-dimethyl-2-imidazolidinone, pyridine, and the like.

The DBU can be substituted with K$_2$CO$_3$, Ca(OH)$_2$, tri-butyl amine, pyridine, and the like.

The process can be conducted using PdX$_2$, PdXL$_2$, Pd(OAc)$_2$, Pd(OAc)$_2$L$_2$, PdCl$_2$(C$_6$H$_5$CN)$_2$, PhPdXL$_2$, PdCl$_2$(COD)$_2$, Pd(acac)$_2$, or PdL$_4$, and the like in an amount of from about 0.005 to about 0.20 per mole of halide.

A skilled practitioner familiar with the above-detailed description of the invention can make many modifications and substitutions without departing from the scope and spirit of the appended claims.

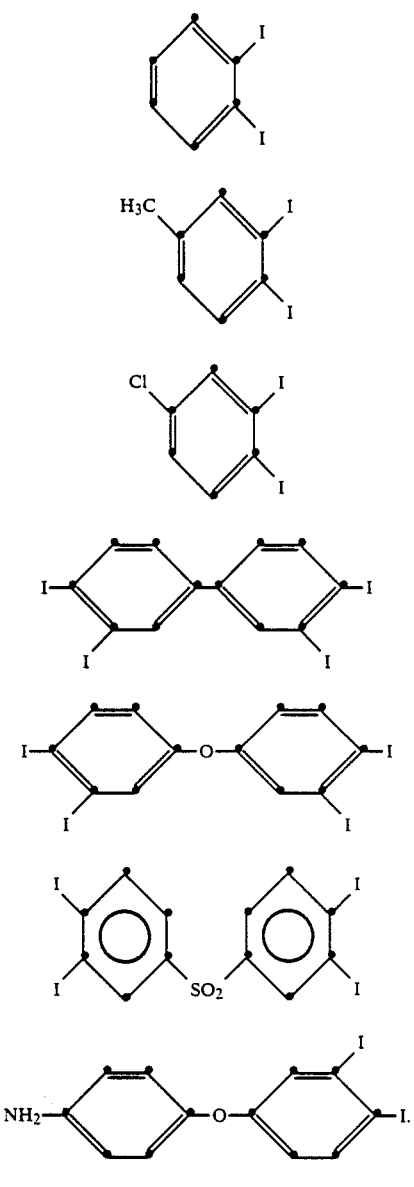

We claim:

1. A process for the preparation of a cyclic imide, said process comprising reacting a vicinal organic halide selected from the class consisting of aryl ortho dihalides and cis-1,2-vinyl dihalides wherein the halogens are selected from bromine and iodine, with a primary amine and carbon monoxide; said process being conducted in the presence of a catalytic quantity of a palladium catalyst, a solvent, and a base to neutralize by-product hydrogen halide;

said aryl dihalide being further characterized by having from 6 to about 20 carbon atoms, said primary amine being selected from primary alkyl and aryl monoamines and diamines, said aryl amines having from 6 to about 20 carbon atoms, said alkyl amines having up to about 10 carbon atoms, said solvent being an ether or a dipolar aprotic solvent, said base being a tertiary amine, and said process being conducted at a temperature of from about ambient to about 250° C.

2. Process of claim 1 wherein said halide is an iodide.

3. Process of claim 2 wherein said organo halide is 1,2-diiodobenzene.

4. Process of claim 2 wherein said halide is 1,2,4,5-tetraiodobenzene.

5. Process of claim 2 wherein said halide is 3,3′,4,4′-tetraiododiphenylsulfone.

6. A process for the preparation of a monomeric cyclic imide, said process comprising reacting (i) vicinal organic halide having only one vicinal dihalide function, and selected from the class consisting of aryl ortho dihalides and cis-1,2-vinyl dihalides wherein the halogens are selected from bromine and iodine with (ii) a primary amine and (iii) carbon monoxide; said process being conducted in the presence of a catalytic quantity of a palladium catalyst, a solvent, and a base to neutralize by-product hydrogen halide;

said aryl dihalide being further characterized by having from 6 to about 20 carbon atoms, said primary amine being selected from primary alkyl and aryl monoamines and diamines, said aryl amines having from 6 to about 20 carbon atoms, said alkyl amines having up to about 10 carbon atoms, said solvent being an ether or a dipolar aprotic solvent, said base being a tertiary amine, and said process being conducted at a temperature of from about ambient to about 250° C.

7. The process of claim 6 wherein aniline is reacted with o-diiodobenzene and CO to produce N-phenylphthalimide.

8. Process of claim 6 wherein n-hexylamine is reacted with o-diiodobenzene and CO to produce N-hexylphthalimide.

9. Process of claim 6 wherein 1,2,4,5-tetraiodobenzene is reacted with CO and m-toluidine to produce N,N'-bis(m-tolyl)pyromellitimide.

10. Process for the preparation of a cyclic imide oligomer or polymer, said process comprising reacting carbon monoxide with an organic halide having two isolated, vicinal dihalo functions independently selected from the class consisting of aryl ortho dihalides and cis-1,2-dihalovinyl functions wherein the halogens are independently selected from bromine and iodine, and with a primary diamine, said process being conducted in the presence of a catalytic quantity of a palladium catalyst, a solvent, and a base to neutralize by-product hydrogen halide;

said aryl dihalide being further characterized by having from 6 to about 20 carbon atoms,
said primary diamine being selected from primary alkyl and aryl diamines, said aryl amines having from 6 to about 20 carbon atoms, said alkyl amines having up to about 10 carbon atoms,
said solvent being an ether or a dipolar aprotic solvent,
said base being a tertiary amine, and
said process being conducted at a temperature of from about ambient to about 250° C.

11. Process of claim 10 wherein said organic halide is 1,2,4,5-tetraiodobenzene, and said diamine is 5-amino-3-(p-aminophenyl)-1,3,3-trimethylindane.

12. Process of claim 10 wherein said organic halide is 1,2,4,5-tetraiodobenzene and said diamine is 1,6-diaminohexane.

13. Process of claim 9 wherein said halide is 3,3',4',4'-tetraiododiphenyl sulfone and said diamine is 5-amino-3-(p-aminophenyl)-1,3,3-trimethylindane.

14. Process of claim 10 wherein said halogens in said organic halide are iodine.

15. Process of claim 13 wherein said process is conducted in the presence of carbon monoxide at a pressure above ambient.

16. Process of claim 10 wherein each paid of vicinal halogens is on the same aromatic ring.

17. Process for the preparation of a cyclic imide, said process comprising reacting carbon monoxide with an organic compound having only one dihalo function selected from aryl ortho dihalide and cis-1,2-dihalovinyl functionalities, and also having only one amino group, said process being conducted in the presence of a catalytic quantity of a palladium catalyst, a solvent, and a base to neutralize by-product hydrogen halide;

said aryl dihalide being further characterized by having from 6 to about 20 carbon atoms,
said solvent being an ether or a dipolar aprotic solvent,
said base being a tertiary amine, and
said process being conducted at a temperature of from about ambient to about 250° C.

18. Process of claim 1 wherein said aryl dihalide is selected from the following compounds: